United States Patent
Kim et al.

(10) Patent No.: US 10,166,223 B2
(45) Date of Patent: Jan. 1, 2019

(54) PHARMACEUTICAL COMPOSITION FOR PREVENTION OR TREATMENT OF DIABETES OR FATTY LIVER COMPRISING CYP4A INHIBITOR

(71) Applicant: KOREA BASIC SCIENCE INSTITUTE, Daejeon (KR)

(72) Inventors: Gun Hwa Kim, Daejeon (KR); Joo Hyun Park, Seoul (KR); Min Ji Lee, Cheongju-si (KR)

(73) Assignee: KOREA BASIC SCIENCE INSTITUTE, Daejeon (KR)

(*) Notice: Subject to any disclaimer, the term of this patent is extended or adjusted under 35 U.S.C. 154(b) by 0 days.

(21) Appl. No.: 15/984,258

(22) Filed: May 18, 2018

(65) Prior Publication Data
US 2018/0333404 A1 Nov. 22, 2018

(30) Foreign Application Priority Data
May 22, 2017 (KR) .......................... 10-2017-0063186

(51) Int. Cl.
| | | |
|---|---|---|
| *A61K 31/4545* | (2006.01) | |
| *A61K 31/538* | (2006.01) | |
| *A61P 1/16* | (2006.01) | |
| *A61P 3/10* | (2006.01) | |

(52) U.S. Cl.
CPC ........ *A61K 31/4545* (2013.01); *A61K 31/538* (2013.01); *A61P 1/16* (2018.01); *A61P 3/10* (2018.01)

(58) Field of Classification Search
CPC ..... A61K 31/4545; A61K 31/538; A61P 3/10; A61P 1/16
See application file for complete search history.

(56) References Cited

U.S. PATENT DOCUMENTS

2009/0163545 A1* 6/2009 Goldfarb .............. A61K 31/122
514/312

OTHER PUBLICATIONS

STN registry database entry 932356-74-6 (entered STN Apr. 25, 2007) (Year: 2007).*
Czech, "Insulin action and resistance in obesity and type 2 diabetes"; Nature Medicine; Jul. 2017; 23(7) : 804-814.
Mayerson et al., "The effects of rosiglitazone on insulin sensitivity, lipolysis, and hepatic and skeletal muscle triglyceride content in patients with type 2 diabetes"; Diabetes, Mar. 2002; 51(3): 797-602.
Petersen et al.,"Reversal of Nonalcoholic Hepatic Steatosis, Hepatic Insulin Resistance, and Hyperglycemia by Moderate Weight Reduction in Patients With Type 2 Diabetes"; Diabetes; Mar. 2015; vol. 54: 603-608.

* cited by examiner

*Primary Examiner* — Dennis Heyer
*Assistant Examiner* — Daniel M Podgorski
(74) *Attorney, Agent, or Firm* — James S. Keddie; Bozicevic, Field & Francis LLP

(57) ABSTRACT

The present invention relates to a pharmaceutical composition for the prevention or treatment of diabetes or fatty liver comprising a CYP4A (cytochrome P450A) inhibitor as an active ingredient. The compound of the present invention has activities of promoting glucose uptake into hepatocytes, inhibiting fat accumulation in liver cells, and inhibiting reactive oxygen production in mitochondria, and thus can be very usefully used for the development of a therapeutic agent for diabetes or fatty liver.

7 Claims, 4 Drawing Sheets

(4 of 4 Drawing Sheet(s) Filed in Color)

PHARMACEUTICAL COMPOSITION FOR PREVENTION OR TREATMENT OF DIABETES OR FATTY LIVER COMPRISING CYP4A INHIBITOR

CROSS-REFERENCE TO RELATED APPLICATIONS

This application claims the benefit of Korean Application Serial No. KR10-2017-0063186, filed on May 22, 2017, which application is incorporated by reference herein.

TECHNICAL FIELD

The present invention relates to a pharmaceutical composition for the prevention or treatment of diabetes or fatty liver comprising a CYP4A (cytochrome P450A) inhibitor as an active ingredient. More specifically, the present invention relates to the composition for the prevention or treatment of diabetes or fatty liver comprising a CYP4A inhibitory compound as an active ingredient that has activities of promoting glucose uptake into hepatocytes, inhibiting fat accumulation in liver cells, and inhibiting active oxygen production in mitochondria.

BACKGROUND OF THE INVENTION

Diabetes is a major factor in disease rates and mortality. Chronic elevated blood sugar levels cause the following complications that make the body debilitate: renal disease, often requiring dialysis or kidney transplantation; peripheral neuropathy; retinopathy leading to blindness; ulcers of the legs and feet resulting in amputation; fatty liver disease that sometimes develops into cirrhosis; and onset of coronary artery disease and myocardial infarction.

There are two main types of diabetes. Type I, or insulin-dependent diabetes mellitus (IDDM), is caused by autoimmune destruction of insulin-producing beta cells of the pancreatic islets. The disease usually occurs in infancy or puberty. Treatment of the disease consists mainly of injecting insulin several times a day. In order to control the dose of insulin, the blood glucose level is tested several times because excess insulin causes hypoglycemia and results in damage to the brain or other functions.

Type II, or noninsulin-dependent diabetes mellitus (NIDDM), typically develops in adults. NIDDM is associated with glucose-using tissues such as adipose tissue, muscle and liver being resistant to the action of insulin. Initially, pancreatic islet beta cells compensate by releasing excess insulin. The ultimate islet β cell failure results in decompensation and chronic hyperglycemia. Conversely, a moderate islet β cell failure may precede or coincide with peripheral insulin resistance. There are several classes of drugs useful in the treatment of NIDDM: 1) an insulin secretagogue that directly stimulates insulin secretion, but at risk of causing hypoglycemia; 2) a dietary insulin secretagogue that enhances glucose-induced insulin secretion but must be ingested before every meal; 3) biguanide including metformin, which inhibits hepatic glucose uptake (which is greatly elevated in diabetes); 4) insulin sensitizers such as thiazolidinedione derivatives rosiglitazone and pioglitazone, which improve peripheral responsiveness to insulin but have side effects such as weight gain, edema and hepatotoxicity; 5) Insulin injection, often required at the end of NIDDM, when islet β cell is failure under chronic hyperstimulation.

Insulin resistance also occurs without significant hyperglycemia and is commonly associated with atherosclerosis, obesity, hyperlipidemia and essential hypertension. The group of abnormal symptoms consists of "metabolic syndrome" or "insulin resistance syndrome". Insulin resistance is also associated with fatty liver, which can develop into chronic inflammation (NASH: "nonalcoholic fatty liver"), fibrosis and cirrhosis. In conclusion, insulin resistance including diabetes is the basis for many of the major factors leading to disease rates and mortality in people over 40 years of age.

Despite the variety of drugs mentioned above, diabetes remains a serious public health problem. Therefore, it is necessary to develop a safe and effective therapeutic agent for diabetes and the fatty liver caused thereby.

SUMMARY

The present invention relates to a pharmaceutical composition for the prevention or treatment of diabetes or fatty liver comprising a CYP4A (cytochrome P450A) inhibitor as an active ingredient. The compound of the present invention has activities of promoting glucose uptake into hepatocytes, inhibiting fat accumulation in liver cells, and inhibiting reactive oxygen production in mitochondria, and thus can be very usefully used for the development of a therapeutic agent for diabetes or fatty liver.

BRIEF DESCRIPTION OF THE DRAWINGS

The patent or application file contains at least one drawing executed in color. Copies of this patent application publication with color drawing(s) will be provided by the U.S. Patent and Trademark Office upon request and payment of the necessary fee.

DETAILED DESCRIPTION OF THE INVENTION

Technical Problem

Figure 1:
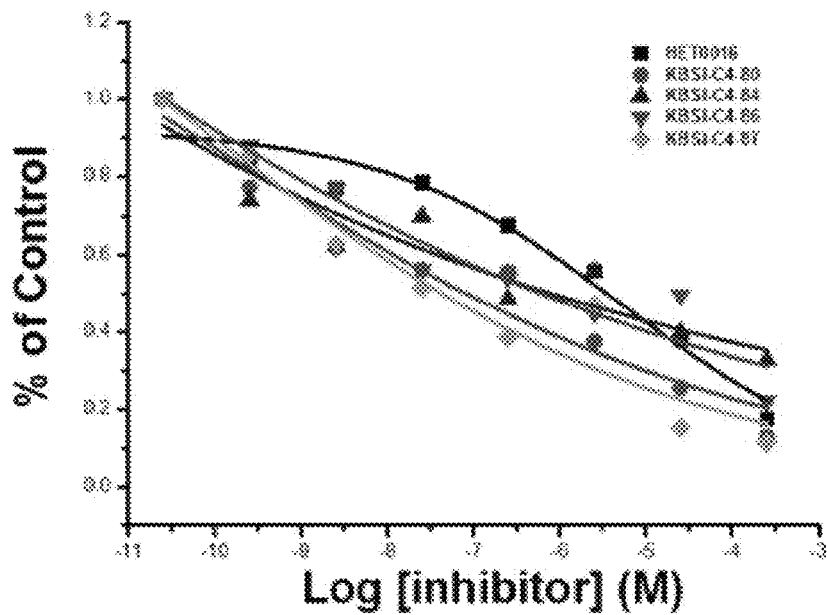
FIG. 1 shows the results of measurement of the inhibitory effect against the activity of CYP4A of the present invention as an emission value. Specifically, when the CYP4A cell lysate is added to the hepatocytes which was cultured with the compound of the present invention and the CYP4A reaction is sufficiently performed, the CYP4A activity inhibition ability of each compound is measured by comparing the emission value of the cells.

Accordingly, as a result of intensive efforts to search for a compound exhibiting the preventive or therapeutic effect on diabetes or fatty liver, the present inventors have completed the present invention after they have found that a group of compounds has activities of promoting glucose uptake into hepatocytes, inhibiting fat accumulation in liver cells, and inhibiting active oxygen production in mitochondria, and thus it can exhibit the preventive or therapeutic effect on diabetes or fatty liver.

Accordingly, an object of the present invention is to provide a pharmaceutical composition for the prevention or treatment of diabetes or fatty liver comprising a compound represented by the following Formula 1 or a pharmaceutically acceptable salt thereof as an active ingredient:

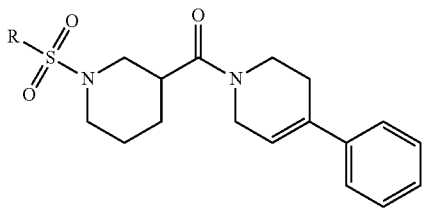

[Formula 1]

wherein

R is phenyl or a 5 or 6 membered heteroaryl containing at least a heteroatom selected from the group consisting of N, O and S, which is unsubstituted or substituted with at least a substituent;

the substituent is at least a substituent selected from the group consisting of linear or branched $C_1$-$C_6$ alkyl; heterocyclic ring or heteroaryl ring containing one or more heteroatoms in the ring and substituted with $C_1$-$C_6$ alkyl or $C_1$-$C_6$ alkylcarbonyl; $C_2$-$C_4$ alkenylene substituted with halogen-substituted phenyl; $C_1$-$C_6$ alkyloxycarbonyl; $C_1$-$C_6$ alkyloxy; halogen; $C_1$-$C_6$ alkyloxy substituted with $C_1$-$C_6$ alkylamino group; hydroxycarbonyl $C_1$-$C_6$ alkyl; $C_1$-$C_6$ alkylamino; phenyl; phenyl substituted with at least a substituent selected from the group consisting of linear or branched $C_1$-$C_6$ alkyl, linear or branched $C_1$-$C_6$ alkyloxy, linear or branched $C_1$-$C_6$ alkyloxycarbonyl, halogen atoms, and alkyl substituted with one or more fluoro atoms; phenoxy; phenoxy substituted with one or more substituents selected from the group consisting of linear or branched $C_1$-$C_6$ alkyl, halogen atoms, and linear or branched $C_1$-$C_6$ alkyloxy; aminosulfonyl; halo; cyano; acetyl; nitro; ethynyl; hydroxy; morpholino; naphthyl; thienyl; pyridyl; tetrahydrofuranyl; indolyl; indolyl substituted with linear or branched $C_1$-$C_6$ alkyloxy; dihydrobenzooxynil; and furylmethylsulfanyl; and the aryl, heterocyclic ring and heteroaryl ring may be a heterocyclic structure in which two or more rings are fused, respectively, and may contain a carbonyl group in the ring.

Another object of the present invention is to provide a method for treating diabetes or fatty liver in a subject in need thereof, the method comprising administering to a subject in need thereof an effective amount of a composition comprising a compound represented by the following Formula 1 or a pharmaceutically acceptable salt thereof as an active ingredient:

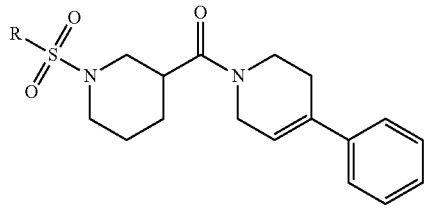

[Formula 1]

wherein

R is phenyl or a 5 or 6 membered heteroaryl containing at least a heteroatom selected from the group consisting of N, O and S, which is unsubstituted or substituted with at least a substituent;

the substituent is at least a substituent selected from the group consisting of linear or branched $C_1$-$C_6$ alkyl; heterocyclic ring or heteroaryl ring containing one or more heteroatoms in the ring and substituted with $C_1$-$C_6$ alkyl or $C_1$-$C_6$ alkylcarbonyl; $C_2$-$C_4$ alkenylene substituted with halogen-substituted phenyl; $C_1$-$C_6$ alkyloxycarbonyl; $C_1$-$C_6$ alkyloxy; halogen; $C_1$-$C_6$ alkyloxy substituted with $C_1$-$C_6$ alkylamino group; hydroxycarbonyl $C_1$-$C_6$ alkyl; $C_1$-$C_6$ alkylamino; phenyl; phenyl substituted with at least a substituent selected from the group consisting of linear or branched $C_1$-$C_6$ alkyl, linear or branched $C_1$-$C_6$ alkyloxy, linear or branched $C_1$-$C_6$ alkyloxycarbonyl, halogen atoms, and alkyl substituted with one or more fluoro atoms; phenoxy; phenoxy substituted with one or more substituents selected from the group consisting of linear or branched $C_1$-$C_6$ alkyl, halogen atoms, and linear or branched $C_1$-$C_6$ alkyloxy; aminosulfonyl; halo; cyano; acetyl; nitro; ethynyl; hydroxy; morpholino; naphthyl; thienyl; pyridyl; tetrahydrofuranyl; indolyl; indolyl substituted with linear or branched $C_1$-$C_6$ alkyloxy; dihydrobenzooxynil; and furylmethylsulfanyl; and the aryl, heterocyclic ring and heteroaryl ring may be a heterocyclic structure in which two or more rings are fused, respectively, and may contain a carbonyl group in the ring.

Technical Solution

An embodiment according to an aspect of the present invention provides a pharmaceutical composition for the prevention or treatment of diabetes or fatty liver comprising a compound represented by the following Formula 1 or a pharmaceutically acceptable salt thereof as an active ingredient:

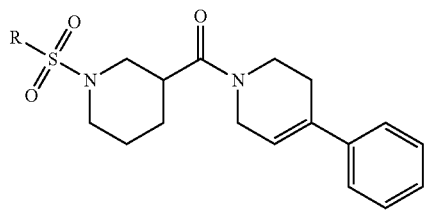

[Formula 1]

wherein

R is phenyl or a 5 or 6 membered heteroaryl containing at least a heteroatom selected from the group consisting of N, O and S, which is unsubstituted or substituted with at least a substituent;

the substituent is at least a substituent selected from the group consisting of linear or branched $C_1$-$C_6$ alkyl; heterocyclic ring or heteroaryl ring containing one or more heteroatoms in the ring and substituted with $C_1$-$C_6$ alkyl or $C_1$-$C_6$ alkylcarbonyl; $C_2$-$C_4$ alkenylene substituted with halogen-substituted phenyl; $C_1$-$C_6$ alkyloxycarbonyl; $C_1$-$C_6$ alkyloxy; halogen; $C_1$-$C_6$ alkyloxy substituted with $C_1$-$C_6$ alkylamino group; hydroxycarbonyl $C_1$-$C_6$ alkyl; $C_1$-$C_6$ alkylamino; phenyl; phenyl substituted with at least a substituent selected from the group consisting of linear or branched $C_1$-$C_6$ alkyl, linear or branched $C_1$-$C_6$ alkyloxy, linear or branched $C_1$-$C_6$ alkyloxycarbonyl, halogen atoms, and alkyl substituted with one or more fluoro atoms; phenoxy; phenoxy substituted with one or more substituents selected from the group consisting of linear or branched $C_1$-$C_6$ alkyl, halogen atoms, and linear or branched $C_1$-$C_6$ alkyloxy; aminosulfonyl; halo; cyano; acetyl; nitro; ethynyl; hydroxy; morpholino; naphthyl; thienyl; pyridyl; tetrahydrofuranyl; indolyl; indolyl substituted with linear or branched $C_1$-$C_6$ alkyloxy; dihydrobenzooxynil; and furylmethylsulfanyl; and the aryl, heterocyclic ring and heteroaryl ring may be a heterocyclic structure in which two or more rings are fused, respectively, and may contain a carbonyl group in the ring.

Another embodiment according to an aspect of the present invention provides a method for treating diabetes or fatty liver in a subject in need thereof, the method comprising administering to a subject in need thereof an effective amount of a composition comprising a compound represented by the following Formula 1 or a pharmaceutically acceptable salt thereof as an active ingredient:

[Formula 1]

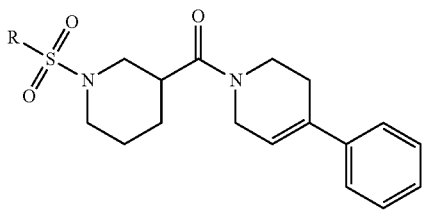

wherein

R is phenyl or a 5 or 6 membered heteroaryl containing at least a heteroatom selected from the group consisting of N, O and S, which is unsubstituted or substituted with at least a substituent;

the substituent is at least a substituent selected from the group consisting of linear or branched $C_1$-$C_6$ alkyl; heterocyclic ring or heteroaryl ring containing one or more heteroatoms in the ring and substituted with $C_1$-$C_6$ alkyl or $C_1$-$C_6$ alkylcarbonyl; $C_2$-$C_4$ alkenylene substituted with halogen-substituted phenyl; $C_1$-$C_6$ alkyloxycarbonyl; $C_1$-$C_6$ alkyloxy; halogen; $C_1$-$C_6$ alkyloxy substituted with $C_1$-$C_6$ alkylamino group; hydroxycarbonyl $C_1$-$C_6$ alkyl; $C_1$-$C_6$ alkylamino; phenyl; phenyl substituted with at least a substituent selected from the group consisting of linear or branched $C_1$-$C_6$ alkyl, linear or branched $C_1$-$C_6$ alkyloxy, linear or branched $C_1$-$C_6$ alkyloxycarbonyl, halogen atoms, and alkyl substituted with one or more fluoro atoms; phenoxy; phenoxy substituted with one or more substituents selected from the group consisting of linear or branched $C_1$-$C_6$ alkyl, halogen atoms, and linear or branched $C_1$-$C_6$ alkyloxy; aminosulfonyl; halo; cyano; acetyl; nitro; ethynyl; hydroxy; morpholino; naphthyl; thienyl; pyridyl; tetrahydrofuranyl; indolyl; indolyl substituted with linear or branched $C_1$-$C_6$ alkyloxy; dihydrobenzooxynil; and furylmethylsulfanyl; and the aryl, heterocyclic ring and heteroaryl ring may be a heterocyclic structure in which two or more rings are fused, respectively, and may contain a carbonyl group in the ring.

Hereinafter, the present invention will be described in more detail.

The present invention provides a pharmaceutical composition for the prevention or treatment of diabetes or fatty liver comprising a compound represented by the following Formula 1 or a pharmaceutically acceptable salt thereof as an active ingredient:

[Formula 1]

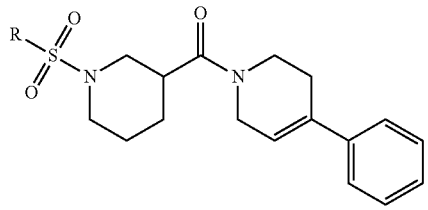

wherein

R is phenyl or a 5 or 6 membered heteroaryl containing at least a heteroatom selected from the group consisting of N, O and S, which is unsubstituted or substituted with at least a substituent; and the substituent is at least a substituent selected from the group consisting of linear or branched $C_1$-$C_6$ alkyl; heterocyclic ring or heteroaryl ring containing one or more heteroatoms in the ring and substituted with $C_1$-$C_6$ alkyl or $C_1$-$C_6$ alkylcarbonyl; $C_2$-$C_4$ alkenylene substituted with halogen-substituted phenyl; $C_1$-$C_6$ alkyloxycarbonyl; $C_1$-$C_6$ alkyloxy; halogen; $C_1$-$C_6$ alkyloxy substituted with $C_1$-$C_6$ alkylamino group; hydroxycarbonyl $C_1$-$C_6$ alkyl; $C_1$-$C_6$ alkylamino; phenyl; phenyl substituted with at least a substituent selected from the group consisting of linear or branched $C_1$-$C_6$ alkyl, linear or branched $C_1$-$C_6$ alkyloxy, linear or branched $C_1$-$C_6$ alkyloxycarbonyl, halogen atoms, and alkyl substituted with one or more fluoro atoms; phenoxy; phenoxy substituted with one or more substituents selected from the group consisting of linear or branched $C_1$-$C_6$ alkyl, halogen atoms, and linear or branched $C_1$-$C_6$ alkyloxy; aminosulfonyl; halo; cyano; acetyl; nitro; ethynyl; hydroxy; morpholino; naphthyl; thienyl; pyridyl; tetrahydrofuranyl; indolyl; indolyl substituted with linear or branched $C_1$-$C_6$ alkyloxy; dihydrobenzooxynil; and furylmethylsulfanyl; and the aryl, heterocyclic ring and heteroaryl ring may be a heterocyclic structure in which two or more rings are fused, respectively, and may contain a carbonyl group in the ring.

In the present invention, the pharmaceutically acceptable salt means a salt or complex of formula (1) having a desired biological activity. Examples of such salts include, but are not limited to, acid addition salts formed with inorganic acid (for example, hydrochloric acid, hydrobromic acid, sulfuric acid, phosphoric acid, and nitric acid), and salts formed with organic acids such as acetic acid, oxalic acid, tartari acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. The compounds may also be administered in pharmaceutically acceptable quaternary salts known to those skilled in the art. In particular, it includes chloride, bromide, iodide, —O-alkyl, toluenesulfonate, methylsulfonate, sulfonate, phosphate, or carboxylate (for example, benzoates, succinates, acetates, glycolates, maleate, malate, fumarates, citrates, tartrates, ascorbates, cinnamoates, mandelate and diphenylacetate). The compounds of formula (1) of the present invention may include not only pharmaceutically acceptable salts, but also all salts, hydrates and solvates which can be prepared by conventional methods.

In addition, the compounds of the present invention may contain one or more asymmetric carbon atoms and may exist in racemic and optically active forms. All such compounds and diastereoisomers are included within the scope of the present invention.

The term "halogen" in the present invention means fluorine, chlorine, bromine and iodine, preferably fluorine, chlorine and bromine.

The term "alkylcarbonyl" in the present invention means a moiety of the formula —R'—R", wherein R' is oxo and R" is alkyl as defined above.

The term "alkyl" in the present invention means, alone or in combination with other groups, a branched or linear monovalent saturated aliphatic hydrocarbon radical of 1 to 20 carbon atoms, preferably 1 to 16 carbon atoms, more preferably 1 to 10 carbon atoms. Lower-alkyl groups as disclosed below are also preferred alkyl groups.

The term "aryl" in the context of the present invention means a monocyclic or heterocyclic aromatic hydrocarbon radical, or more specifically the group of the specific compounds described in the examples. It is understood that these radicals can be categorized into the group encompassing these radicals as well as the radicals described in the first or second priority or the two priorities, wherein said radicals are substituted by one or more substituents, preferably one, two, or three substituents independently selected from the group consisting of alkyl, hydroxy, alkoxy, haloalkyl, haloalkoxy, Y—C(O)—R (at this time, Y is absent or is an alkylene group, and R is hydrogen, alkyl, haloalkyl, haloalkoxy, hydroxy, alkoxy, amino, monoalkylamino or dialkylamino), heteroalkyl, heteroalkyloxy, heteroalkylamino, halo, nitro, cyano, amino, monoalkylamino, dialkylamino, alkylsulfonylamino, heteroalkylsulfonylamino, sulfonamido, methylenedioxy, ethylenedioxy, heterocycle, or heterocyclylalkyl, or more specifically the group of the specific compounds described in the examples. It is understood that these radicals can be categorized into a group encompassing these radicals as well as radicals described in the first or second priority or the two priorities. More specifically, the term aryl includes phenyl, chlorophenyl, methoxyphenyl, 2-fluorophenyl, 2, 4-difluorophenyl, 1-naphthyl, 2-naphthyl and their derivatives, but is not limited to.

The term "heteroaryl" as used herein refers to a monocyclic or multicyclic aromatic ring system. As heterocyclyl radicals defined above in an aromatic form, in certain embodiments, one or more of about 5 to about 20 atoms, or in one embodiment, 1 to 5 atoms are heteroatoms in the ring system. Thus, non-limiting examples as elements other than carbon include nitrogen, oxygen, or sulfur. The heteroaryl groups may selectively be fused to form a benzene ring. Heteroaryl radicals can be attached to the main structure at any heteroatom or carbon atom and thereby produce stable compounds. Non-limiting examples of such heteroaryl radicals include acridinyl, benzimidazolyl, benzindolyl, benzisoxazinyl, benzo [4,6] imidazo [1,2-a]pyridinyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, 3-carbonyl, carbazolyl, cinnolinyl, dibenzofuranyl, furanyl, imidazolyl, imidazopyridinyl, imidazothiazoly, Indazolyl, indolizinyl, indolyl, isobenzothienyl, isoindolinyl, isoquinolinyl, isothiazolidinyl, isothiazolyl, naphthyridinyl, octahydroindolyl, octahydroisoindolyl, oxazolidinonyl, oxazolidinyl, oxazolopyridinyl, oxazolyl, isoxazolyl, oxiranyl, perimidinyl, phenanthridinyl, phenanthrolinyl, phenarsazinyl, phenazinyl, phenothiazinyl, phenoxazinyl, phthalazinyl, pteridinyl, furinyl, pyrazinyl, pyrazolyl, pyridazinyl, pyridinyl, pyridopyridinyl, pyrimidinyl, pyrrolyl, quinazolinyl, quinolinyl, quinoxalinyl, tetrazolyl, thiadiazolyl, thiazolyl, thienyl, triazinyl and triazolyl.

The term "alkenylene" or "alkenylene chain" in the present invention is linear or branched unsaturated divalent radicals consisting of solely of carbon and hydrogen atoms, and having from 2 to 8 carbon atoms, the unsaturation only exists as a double bond, and a double bond may be present between any two carbon atoms in the chain. Examples thereof include ethenylene, prop-1-ethylene, and boot-2-ethylene. The alkenylene chain can be attached to the remainder of the molecule through any two carbon atoms in the chain.

Preferably, in the present invention, the compound of Formula 1 may be selected from among compounds having the following structures:

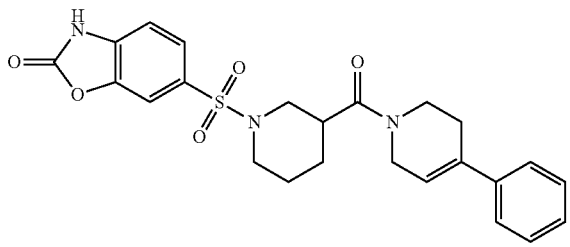

[Formula 2] (Candi #8-0)

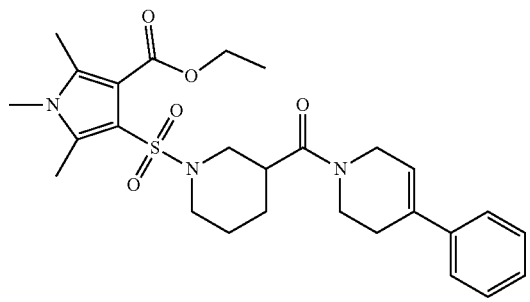

[Formula 3] (Candi #8-1)

-continued

[Formula 4] (Candi #8-2)
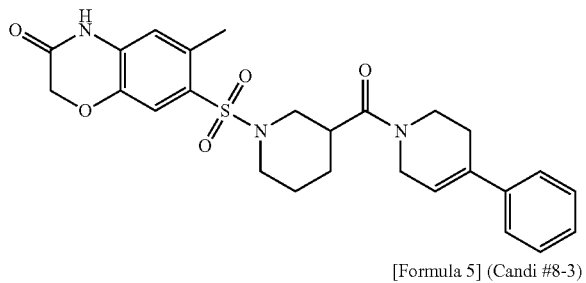

[Formula 5] (Candi #8-3)
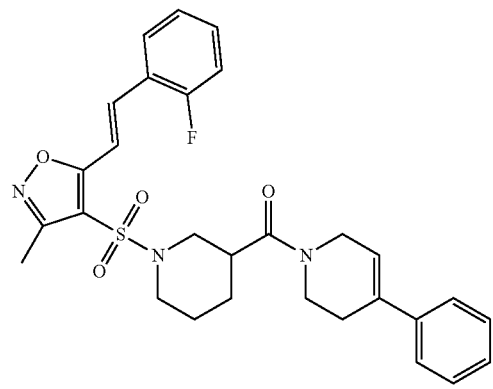

[Formula 6] (Candi #8-4)
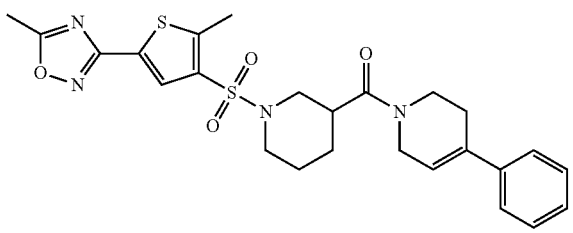

[Formula 7] (Candi #8-5)
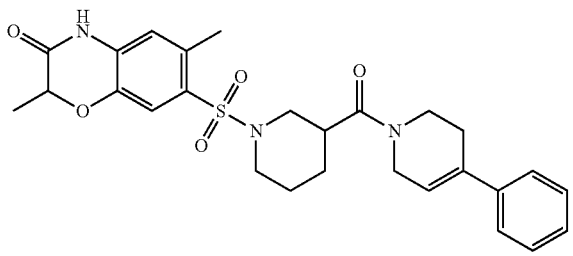

[Formula 8] (Candi #8-6)
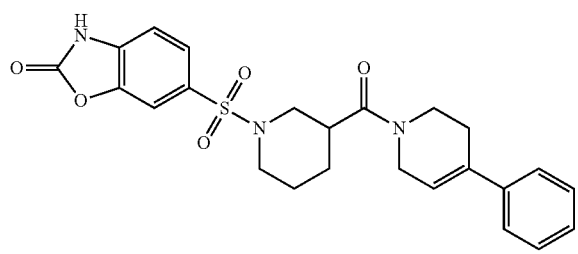

-continued

[Formula 9] (Candi #8-7)
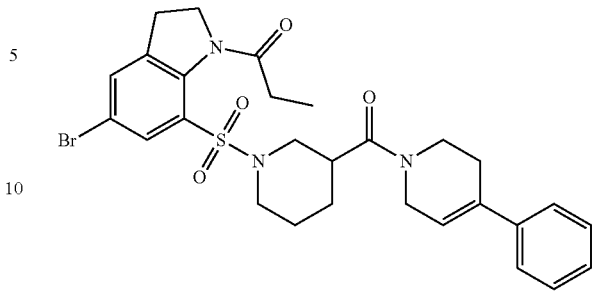

[Formula 10] (Candi #8-8)
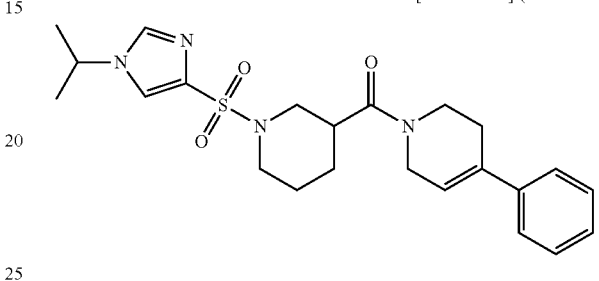

The present inventors have confirmed through previous studies that the inhibition of CYP4A (cytochrome P450 4A) is a potent therapeutic target for endoplasmic reticulum (ER) stress induced hepatic insulin resistance and apoptosis. Accordingly, it has been confirmed that the inhibitor of the enzyme can be used as a pharmaceutical composition for the prevention or treatment of diabetes or fatty liver derived from obesity. In addition, it has been confirmed that the CYP4A inhibitor can exhibit such effect through the mechanism of suppressing the ER stress, decreasing the blood insulin concentration, and inhibiting the cell death of the liver cell (Korean Patent No. 10-1235811).

Accordingly, the present inventors selected compounds of the above formula (1) having CYP4A inhibitory activity through screening compound libraries, and experimentally confirmed that these compounds can exhibit preventive or therapeutic effects on diabetes or fatty liver.

As used herein, the term "treatment" or "treating" means, unless otherwise stated, reversing, alleviating, inhibiting or preventing the disease or disorder to which the term applies, or one or more symptoms of the disease or disorder.

In the present invention, 'diabetes' is a chronic disease characterized by abnormal glucose metabolism. The diabetes is caused by the result of the absolute production deficiency of insulin (insulin-dependent diabetes mellitus or type I diabetes), which is the most important hormone that regulates blood glucose concentration, or the result of insulin action reduction in target organs (non-insulin dependent diabetes mellitus or type II diabetes).

Preferably, in the present invention, diabetes refers to non-insulin dependent diabetes mellitus (type II diabetes mellitus). Such non-insulin dependent diabetes mellitus generally exhibits abnormality of glucose metabolism and lipid metabolism. That is, in the case of the non-insulin-dependent diabetes mellitus, insulin secretion is delayed or insufficient after food ingestion, so that the sugar production in the liver is not reduced and the utilization rate of glucose by the peripheral tissues such as muscle, liver and fat is not increased. The resulting postprandial hyperglycemia symptoms always promote insulin secretion, resulting in chronic insulin hypertrophy, and if this condition continues, beta cells can no longer maintain the increased insulin secretion rate, resulting in insulin resistance. Continuous insulin resistance causes problems with insulin production and leads to hypoinsulinemia. In particular, decreased insulin ratio to glucagon increases glyconeogenesis in the liver.

In addition, an increase in free fatty acids in the blood is suggested as a cause of insulin resistance. The increase in free fatty acids in the blood suppresses insulin-induced glucose utilization in peripheral tissues and increases blood glucose levels by interfering with the inhibition of glyconeogenesis in the liver tissue. In the non-insulin dependent diabetes mellitus, in addition to the increase in free fatty acid in the blood, an increase in blood cholesterol and triglyceride and a decrease in HDL-cholesterol are observed. The incidence of such a dyslipidemia is 2 to 4 times higher than that of a normal person.

In diabetes mellitus and diabetic complications, diabetes mellitus is closely related to oxidative stress. Chronic hyperglycemia in diabetes mellitus increases the production of free radicals by various pathways such as autoxidation of glucose and protein saccharification, and oxidative stress is increased by these highly reactive substances. Furthermore, antioxidant enzyme expression and activity are inadequate to prevent oxidative stress induced by hyperglycemia, resulting in an abnormally increased antioxidant enzyme activity, thereby destroying the balance state maintained between these enzymes.

In an embodiment of the present invention, it has been confirmed that the compounds of formula (1) can alleviate oxidative stress due to diabetes and high blood sugar. That is, the compounds of formula (1) showed effects of promoting blood glucose uptake into hepatocytes and inhibiting the generation of reactive oxygen species in the mitochondria.

Meanwhile, in the present invention, the "fatty liver" is caused by the accumulation of fat in the liver due to excessive fat or alcohol consumption, increased fat synthesis in the liver, reduction of triglyceride emissions and combustion. Generally, when the proportion of fat accumulated in the liver is 5% or more, it is defined as fatty liver. Most of the fat accumulated in the liver is triglyceride.

Fatty liver can be divided into alcoholic fat liver due to overdrinking and non-alcoholic fatty liver due to obesity, diabetes, hyperlipidemia or drugs. Alcoholic fatty liver is caused by excessive intake of alcohol, which promotes fat synthesis in the liver and does not result in normal energy metabolism. Non-alcoholic fatty liver disease, on the other hand, is common in people suffering from obesity, insulin hypersensitivity, and diabetes. This phenomenon suggests that nonalcoholic fatty liver may be caused by increased concentration of free fatty acids in the blood due to insulin resistance or excessive fat decomposition (A. B. Mayerson et al., Diabetes, 51: 797-802 (2002); K. F. Petersen et al., Diabetes, 54: 603-608 (2005)).

In the present invention, the fatty liver may be any one or more selected from the group consisting of an alcoholic fatty liver, a nonalcoholic fatty liver, a nutritive fatty liver, a starvation fatty liver, an obese liver fat, and a diabetic fatty liver, and most preferably diabetic fatty liver, but is not limited thereto.

According to an embodiment of the present invention, the compound of formula (1) inhibits the accumulation of fat in liver cells, and thus it is possible to exhibit preventive or therapeutic effects on fatty liver.

In the pharmaceutical composition according to the present invention, the compound of formula (1) or a pharmaceutically acceptable salt thereof may be administered orally or parenterally in various formulations at the time of clinical administration. In the case of formulation, a diluent or excipient such as commonly used filler, an extender, a binder, a wetting agent, a disintegrant, or a surfactant may be used.

Solid form preparations for oral administration include tablets, patients, powders, granules, capsules, and troches, which may be prepared by mixing one or more excipients such as starch, calcium carbonate, sucrose, lactose, or gelatin in the compound of formula (1) or a pharmaceutically acceptable salt thereof of the present invention. In addition to simple excipients, lubricants such as magnesium stearate, and talc may also be used. Liquid preparations for oral administration include suspensions, solutions, emulsions or syrups. In addition to commonly used diluents such as water and liquid paraffin, various excipients such as wetting agents, sweetening agents, fragrances, and preservatives may be included.

Formulations for parenteral administration include sterile aqueous solutions, non-aqueous solutions, suspensions, emulsions, freeze-dried agents and suppositories. Examples of the non-aqueous solvent and suspending agent include propylene glycol, polyethylene glycol, vegetable oil such as olive oil, and injectable ester such as ethyl oleate. Witepsol, macrogol, tween 61, cacao paper, laurin, glycerol, and gelatin may be used as a base for suppositories.

The dosage of the compound of formula (1) or a pharmaceutically acceptable salt thereof of the present invention to the human body may vary depending on the patient's age, weight, sex, dosage form, health condition and disease severity. It is generally from 0.1 to 1000 mg/day, preferably from 1 to 500 mg/day, based on adult patients weighing 70 Kg, and it may also be administered once or several times a day at certain intervals according to the judgment of a doctor or pharmacist.

The pharmaceutical composition of the present invention can be used alone or in combination with methods using surgery, hormone therapy, chemotherapy and biological response modifiers.

Meanwhile, the compound according to the present invention can be formulated into various forms according to the purpose.

Formulation examples for the composition of the present invention are illustrated below.

<Formulation Example 1> Preparation of Pharmaceutical Agent

1. Manufacturing of Powder 2 g of the compound of formula (1) according to the present invention 1 g of Lactose The above components were mixed and packed in airtight bags to prepare powders.

2. Preparation of Tablets 100 mg of the compound of formula (1) according to the present invention 100 mg of corn starch 100 mg of milk 2 [0161] Mg of Magnesium Stearate After mixing the above components, tablets were prepared by tableting according to a conventional method for producing tablets.

3. Preparation of Capsules 100 mg of the compound of formula (1) according to the present invention 100 mg of corn starch 100 mg of milk 2 mg of magnesium stearate After mixing the above components, the capsules were filled in gelatin capsules according to the conventional preparation method of capsules.

4. Manufacture of Rings 1 g of the compound of formula (1) according to the invention
1.5 g of Lactose
1 g of Glycerin
0.5 g of xylitol After mixing the above components, they were prepared to be 4 g per one ring according to a conventional method.

5. Manufacture of Granules 150 mg of the compound of formula (1) according to the present invention
50 mg of Soybean extract 50 mg
200 mg of glucose
600 mg of starch After mixing the above components, 100 mg of 30% ethanol was added and the mixture was dried at 60° C. to form granules, which were then filled in a capsule.

In addition, the present invention provides a method for treating diabetes or fatty liver in a subject in need thereof, the method comprising administering to a subject in need thereof an effective amount of a composition comprising a compound represented by the following Formula 1 or a pharmaceutically acceptable salt thereof as an active ingredient:

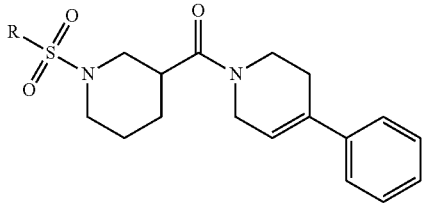

[Formula 1]

wherein

R is phenyl or a 5 or 6 membered heteroaryl containing at least a heteroatom selected from the group consisting of N, O and S, which is unsubstituted or substituted with at least a substituent;

the substituent is at least a substituent selected from the group consisting of linear or branched $C_1$-$C_6$ alkyl; heterocyclic ring or heteroaryl ring containing one or more heteroatoms in the ring and substituted with $C_1$-$C_6$ alkyl or $C_1$-$C_6$ alkylcarbonyl; $C_2$-$C_4$ alkenylene substituted with halogen-substituted phenyl; $C_1$-$C_6$ alkyloxycarbonyl; $C_1$-$C_6$ alkyloxy; halogen; $C_1$-$C_6$ alkyloxy substituted with $C_1$-$C_6$ alkylamino group; hydroxycarbonyl $C_1$-$C_6$ alkyl; $C_1$-$C_6$ alkylamino; phenyl; phenyl substituted with at least a substituent selected from the group consisting of linear or branched $C_1$-$C_6$ alkyl, linear or branched $C_1$-$C_6$ alkyloxy, linear or branched $C_1$-$C_6$ alkyloxycarbonyl, halogen atoms, and alkyl substituted with one or more fluoro atoms; phenoxy; phenoxy substituted with one or more substituents selected from the group consisting of linear or branched $C_1$-$C_6$ alkyl, halogen atoms, and linear or branched $C_1$-$C_6$ alkyloxy; aminosulfonyl; halo; cyano; acetyl; nitro; ethynyl; hydroxy; morpholino; naphthyl; thienyl; pyridyl; tetrahydrofuranyl; indolyl; indolyl substituted with linear or branched $C_1$-$C_6$ alkyloxy; dihydrobenzooxynil; and furylmethylsulfanyl; and the aryl, heterocyclic ring and heteroaryl ring may be a heterocyclic structure in which two or more rings are fused, respectively, and may contain a carbonyl group in the ring.

The term "treatment or treating" as used herein is a concept involving inhibition, elimination, alleviation, relief, amelioration and/or prevention of a disease itself, or symptoms or conditions caused by the disease.

The "effective amount" as used herein refers to an amount that, when administered to an individual, represents an improvement, treatment, or prevention effect of diabetes or fatty liver. It is obvious to those skilled in the art that the therapeutically effective amount may be determined within the scope of sound medical judgment. Preferably, the specific therapeutically effective amount for a particular patient may vary depending on a variety of factors including the type and degree of a desired reaction, the specific composition including the use of any other agents according to the intended use, the patient's age, weight, general health condition, gender, diet, administration time, administrate route and excretion rate of the composition, duration of treatment, other drugs used in combination or coincidentally with the specific composition, and like factors well known in the medical arts. Therefore, preferably, the effective amount of the composition suitable for the purpose of the present invention is determined in consideration of the foregoing.

The term "subject" refers to an animal, preferably a mammal which especially includes a human, while including animal-derived cells, tissues, organs and the like. The subject may be a patient in need of the above mentioned effect.

Advantageous Effect

The compound of formula (1) of the present invention has activities of promoting glucose uptake into hepatocytes, inhibiting fat accumulation in liver cells, and inhibiting reactive oxygen production in mitochondria, and can be very useful for the development of a therapeutic agent for diabetes or fatty liver.

MODE FOR CARRYING OUT INVENTION

Hereinafter, the present invention will be described in detail. However, the following examples are illustrative of the present invention, and the present invention is not limited to the following examples.

Example 1

Selection of Compounds Exhibiting CYP4A Inhibitory Activity

The present inventors screened CYP4A inhibitors through screening of commercially available compound libraries based on the contents of the prior art that a compound exhibiting CYP4A inhibitory activity could have preventive or therapeutic effects on diabetes or fatty liver.

CYP4A11 DNA was inserted into human hepatocyte HepG$_2$ cells by transfection and cultured in an incubator for 24 hours to express the protein. After that, the cells were pulverized by adding RIPA buffer (20 mM Tris-HCl (pH 7.5), 150 mM NaCl, 1 mM Na$_2$EDTA, 1 mM EGTA, 1% NP-40, 1% sodium deoxycholate, 2.5 mM sodium pyrophosphate, 1 mM b-glycerophosphate, 1 mM Na$_3$VO$_4$, 1 μg/ml leupeptin), and then the CYP4A activity experiment was carried out by the following method.

First, a compound having CYP4A inhibitory activity was mixed with water by concentration in a 96-well plate (white opaque polystyrene nontreated flat-bottom well), and 1 M KPO$_4$ buffer (13.94 g K$_2$HPO$_4$, 2.72 g KH$_2$PO$_4$, based on 100 ml), 5 mM Luciferin-4A, and 1 pmol CYP4A cell lysate were added and incubated at room temperature for 10 minutes. After adding the NADPH Regeneration system (20× sol.A, 100× sol.B in water, Cal. No. D399, Thermo Fisher SCIENTIFIC), the reaction was allowed to proceed for 1 hour at room temperature to allow enough reaction of CYP4A, and the CYP4A reaction was terminated by adding the Luciferin Detection reagent. A luminescent reaction was induced and allowed to react at room temperature for 20 minutes. The degree of inhibition of CYP4A activity was measured by comparing the emission values from each well with a microplate reader.

Figure 2:
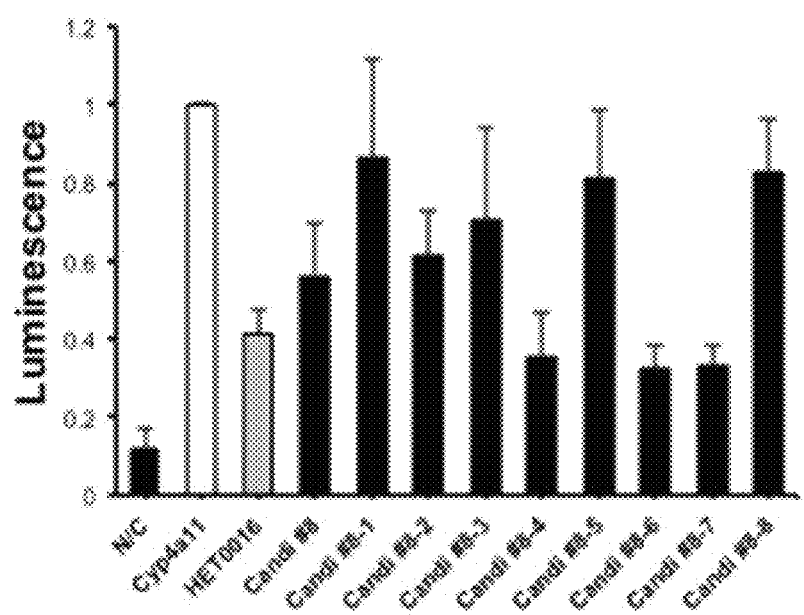
FIG. 2 shows the results of measuring the degree of inhibition of CYP4A activity by comparing the emission value of compounds showing CYP4A inhibitory activity.

As a result, as shown in FIG. 1 and FIG. 2, it was confirmed that the compounds of formulas (2) to (10) of the present invention has an inhibitory effect on CYP4A. In addition, the screened compounds were found to exhibit better IC50 values than the known CYP4A specific inhibitor HET0016 (N-hydroxy-N'-(4-butyl-2-methylphenyl)-formamidine).

Example 2

Promoting Effect on Glucose Uptake

Human hepatocellular HepG2 cells were cultured in high glucose DMEM (Dulbecco's medium Eagle's medium, glucose 25 mM) medium containing 10% FBS (fetal bovine serum), and glucose uptake experiments were performed as follows.

First, HepG2 cells were cultured in a 96-well plate (clear bottom culture plate) at 1×10$^4$ cells/well. And then, 5 μM of each compound showing CYP4A inhibitory activity was added, followed by incubation for 6 hours. After adding thapsigargin or tunicamycin, ER stress inducing substances, to the above plate, it was incubated for 24 hours in a 37° C. incubator. After that, insulin and 2-NBDG (2-(N-(7-Nitrobenz-2-oxa-1,3-diazol-4-yl) Amino)-2-Deoxyglucose were added and reacted in a 37° C. incubator for 3 hours. After washing with PBS (phosphate buffered saline), fluorescence was measured with a microplate reader croplate reader (excitation: 488 nm, emission: 508 nm).

Figure 3:
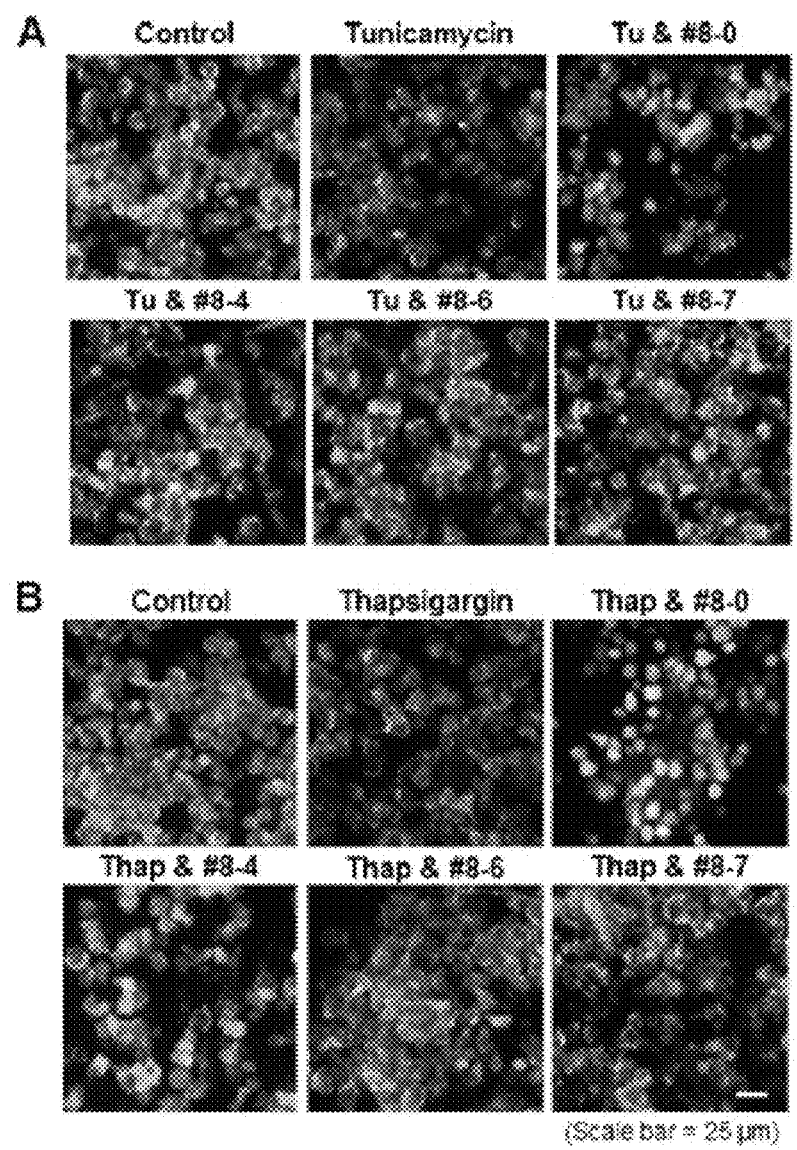
FIG. 3 shows the result of confirming glucose absorption promoting effect of the present invention with fluorescence. Specifically, hepatocyte which was cultured with the compounds of the present invention were reacted with thapsigargin or tunicamycin, the endoplasmic reticulum (ER) stress inducing substances, followed by the reaction with insulin and 2-NBDG to confirm the glucose absorption promoting effect of the compounds of the present invention (Excitation: 488 nm, Emission: 508 nm).

As a result, as shown in FIG. 3, in the test group treated with the compounds of the present invention, the glucose uptake was promoted to a similar degree as the positive control group, but control cells treated with thapsigargin or tunicamycin were found to be highly inhibited in glucose uptake compared with the compounds of the present invention and the positive control.

Example 3

Inhibitory Activity on Fat Accumulation in Hepatocytes

Human hepatocellular HepG2 cells were cultured in high glucose DMEM (Dulbecco's medium Eagle's medium, glucose 25 mM) medium containing 10% FBS (fetal bovine serum), and fat accumulation was measured by the following method.

First, HepG2 cells were cultured in a 96-well (black clear bottom culture plate) at 5×10$^3$ cells/well. And then, 5 μM of a compound showing CYP4A inhibitory activity was added, followed by incubation for 6 hours. Here, palmitate, a fatty acid that induces fat accumulation in hepatocytes, is added and incubated for 72 hours in a 37° C. incubator. Subsequently, 4% paraformaldehyde was added and allowed to react at room temperature for 15 minutes. Nile red solution was then added, and the reaction was carried out at 37° C. for 10 minutes under light blocking. At the end of the reaction time, fluorescence was measured with a microplate reader (excitation: 530 nm, emission: 635 nm).

Figure 4:
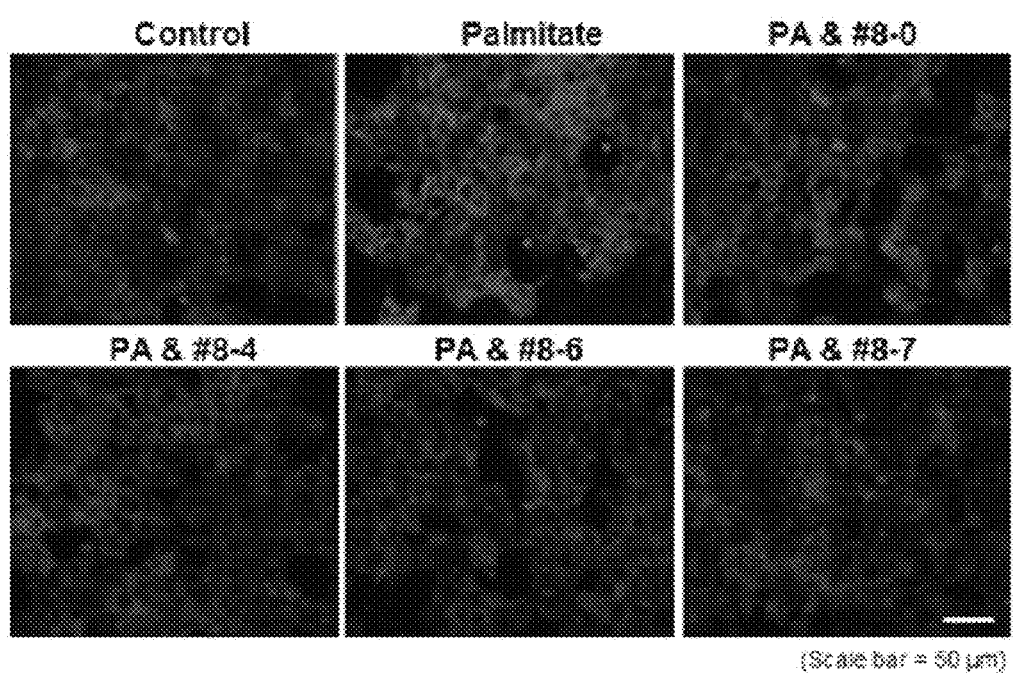
FIG. 4 shows the results showing the inhibitory activity on fat accumulation in hepatocytes of the present invention. Specifically, when hepatocyte which was cultured with the compounds of the present invention were reacted with palmitate, fatty acid accumulation inducing substance, the lipid accumulation inhibitory activity was confirmed by fluorescence (excitation: 530 nm, emission: 635 nm).

As a result, as shown in FIG. 4, in the test group treated with the compounds of the present invention, the fat accumulation in liver cells was inhibited to a similar degree as in the positive control group. On the other hand, in the case of the cells reacted with the fatty acid palmitate, fat accumulation inducing substance, it was possible to confirm the accumulation of fat in a large amount compared with the compounds of the present invention and the positive control.

Example 4

Reactive Oxygen Scavenging Ability

HepG2 cells, a human liver cell line, were cultured in high glucose DMEM (Dulbecco's medium Eagle's medium, glucose 25 mM) medium containing 10% FBS (fetal bovine serum) and experiments were performed to measure the oxygen scavenging ability in the following method.

First, HepG2 cells were cultured in a 96-well (black clear bottom culture plate) at 1×10$^4$ cells/well, And then, 5 μM of a compound showing CYP4A inhibitory activity was added, followed by incubation for 6 hours. After adding thapsigargin or tunicamycin, ER stress inducing substances, to the above plate, it was incubated for 24 hours in a 37° C. incubator. After that, 5 μM H$_2$DCFDA (cell-permeant 2', 7'-dichlorodihydrofluorescein diacetate) was added and reacted in a 37° C. incubator for 30 minutes. After washing with PBS, it was placed in a 37° C. incubator for 30 minutes and waited for the luminescence to occur. The fluorescence was then measured with a microplate reader (excitation: 488 nm, emission: 508 nm).

Figure 5:
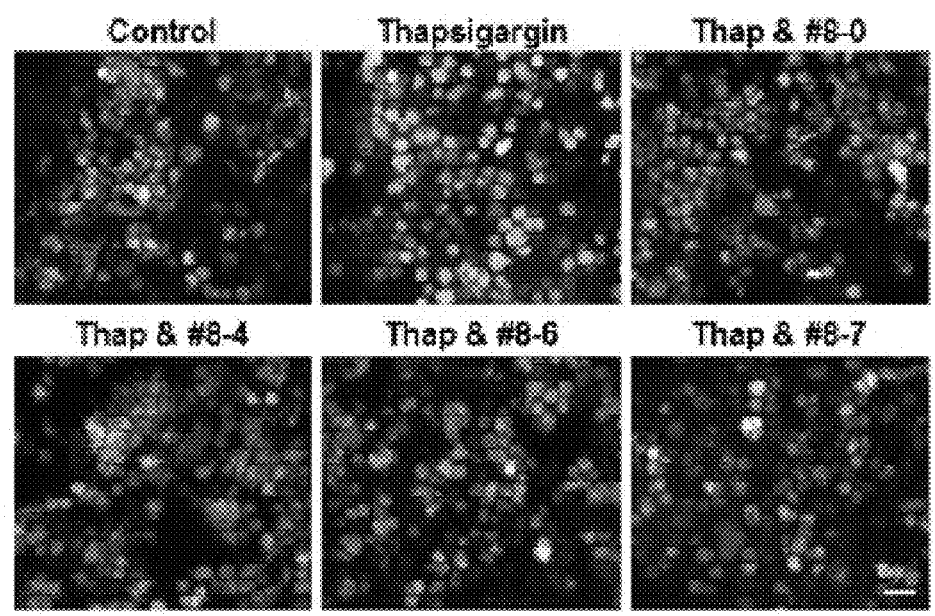
FIG. 5 shows the results of showing the reactive oxygen scavenging ability of the compounds of the present invention. Specifically, hepatocyte which was cultured with the compounds of the present invention were reacted with thapsigargin or tunicamycin, the endoplasmic reticulum (ER) stress inducing substances, the reactive oxygen scavenging ability was confirmed by fluorescence (Excitation: 488 nm, Emission: 508 nm)
Figure 5:
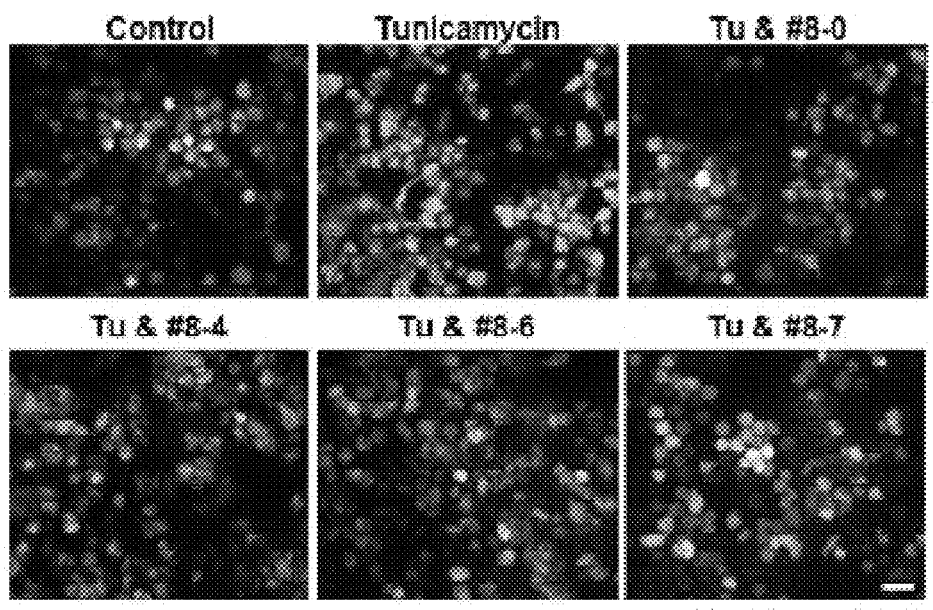

As a result, as shown in FIG. 5, in the test group treated with the compounds of the present invention, the removal of reactive oxygen was promoted to a similar degree as the positive control group. On the other hand, in the case of the cells that were reacted with thapsigargin or tunicamycin, ER stress inducing substances, it was confirmed that the effect of removing the reactive oxygen was insufficient compared with the compounds of the present invention and the positive control.

INDUSTRIAL APPLICABILITY

The compound of formula (1) of the present invention has activities of promoting glucose uptake into hepatocytes, inhibiting fat accumulation in liver cells, and inhibiting reactive oxygen production in mitochondria, and can be very useful for the development of a therapeutic agent for diabetes or fatty liver, and is highly industrially applicable.

What is claimed is:

1. A method for treating diabetes or fatty liver in a subject in need thereof, the method comprising administering to a subject in need thereof an effective amount of a composition comprising a compound represented by the following Formula 1 or a pharmaceutically acceptable salt thereof as an active ingredient:

[Formula 1]

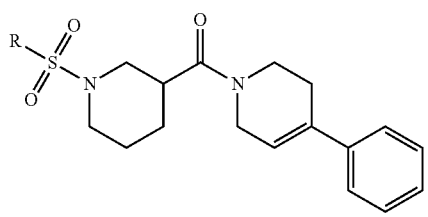

wherein

R is phenyl or a 5 or 6 membered heteroaryl containing at least a heteroatom selected from the group consisting of N, O and S, which is unsubstituted or substituted with at least a substituent;

the substituent is at least a substituent selected from the group consisting of linear or branched $C_1$-$C_6$ alkyl; heterocyclic ring or heteroaryl ring containing one or more heteroatoms in the ring and substituted with $C_1$-$C_6$ alkyl or $C_1$-$C_6$ alkylcarbonyl; $C_2$-$C_4$ alkenylene substituted with halogen-substituted phenyl; $C_1$-$C_6$ alkyloxycarbonyl; $C_1$-$C_6$ alkyloxy; halogen; $C_1$-$C_6$ alkyloxy substituted with $C_1$-$C_6$ alkylamino group; hydroxycarbonyl $C_1$-$C_6$ alkyl; $C_1$-$C_6$ alkylamino; phenyl; phenyl substituted with at least a substituent selected from the group consisting of linear or branched $C_1$-$C_6$ alkyl, linear or branched $C_1$-$C_6$ alkyloxy, linear or branched $C_1$-$C_6$ alkyloxycarbonyl, halogen atoms, and alkyl substituted with one or more fluoro atoms; phenoxy; phenoxy substituted with one or more substituents selected from the group consisting of linear or branched $C_1$-$C_6$ alkyl, halogen atoms, and linear or branched $C_1$-$C_6$ alkyloxy; aminosulfonyl; halo; cyano; acetyl; nitro; ethynyl; hydroxy; morpholino; naphthyl; thienyl; pyridyl; tetrahydrofuranyl; indolyl; indolyl substituted with linear or branched $C_1$-$C_6$ alkyloxy; dihydrobenzooxynil; and furylmethylsulfanyl; and the aryl, heterocyclic ring and heteroaryl ring may be a heterocyclic structure in which two or more rings are fused, respectively, and may contain a carbonyl group in the ring.

2. The method of claim 1, wherein the compound of Formula 1 is any one selected from the following Formula 2 to 10:

[Formula 2]

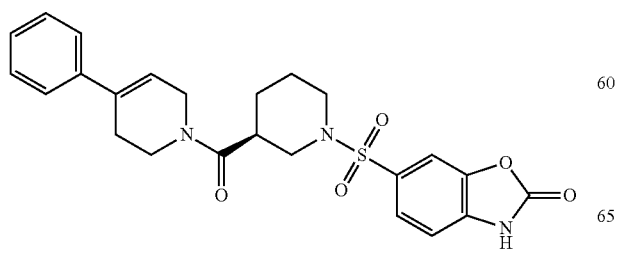

[Formula 3]

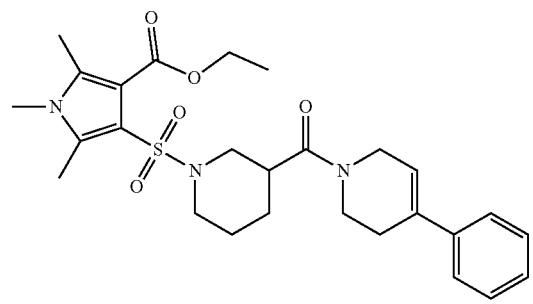

[Formula 4]

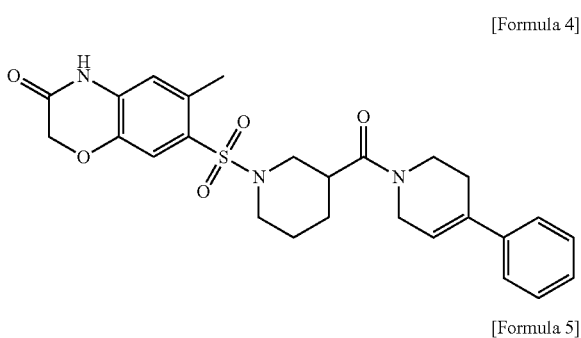

[Formula 5]

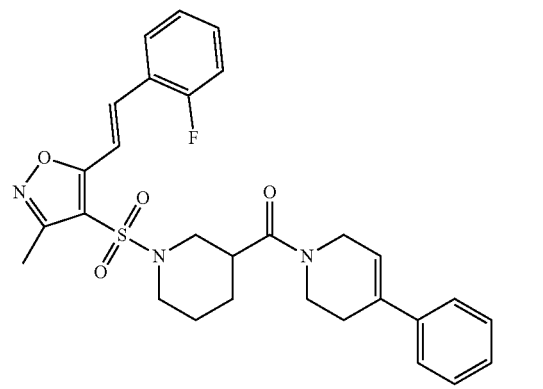

[Formula 6]

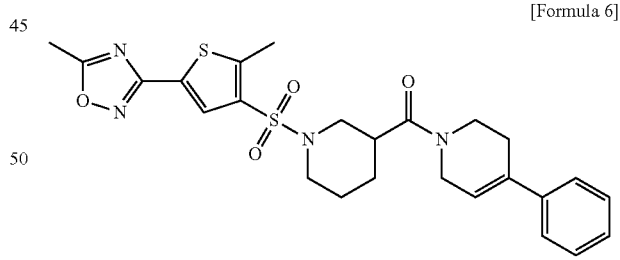

[Formula 7]

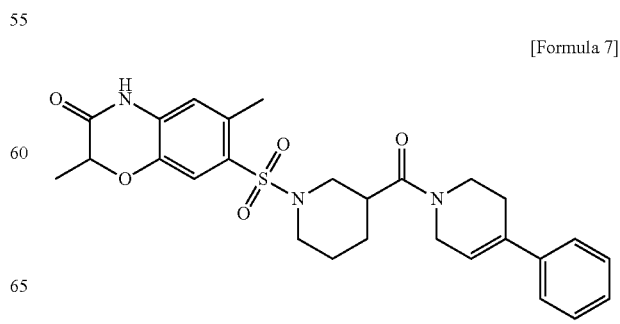

[Formula 8]

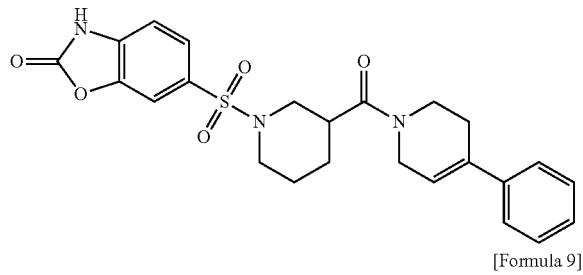

[Formula 9]

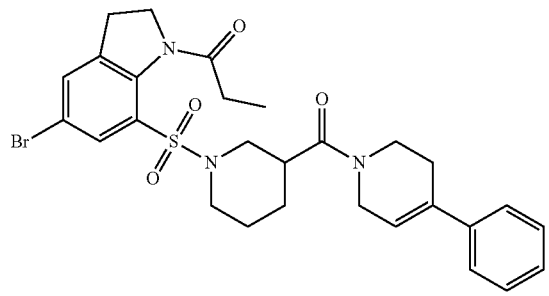

[Formula 10]

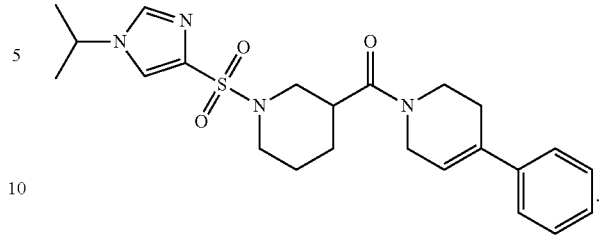

3. The method of claim 1, wherein the diabetes is type 2 diabetes.

4. The method of claim 1, wherein the subject is obese.

5. The method of claim 1, wherein the compound has an effect of enhancing glucose uptake in the liver.

6. The method of claim 1, wherein the compound has an activity of inhibiting the production of reactive oxygen in mitochondria.

7. The method of claim 1, wherein the subject has type 2 diabetes and fatty liver.

* * * * *